(12) United States Patent
Matlin

(10) Patent No.: US 7,195,185 B2
(45) Date of Patent: Mar. 27, 2007

(54) SHREDDER WITH SEPARATE WASTE OPENING

(75) Inventor: Tai Hoon Kim Matlin, Round Lake Beach, IL (US)

(73) Assignee: Fellowes, Inc., Itasca, IL (US)

( * ) Notice: Subject to any disclaimer, the term of this patent is extended or adjusted under 35 U.S.C. 154(b) by 21 days.

(21) Appl. No.: 10/978,482

(22) Filed: Nov. 2, 2004

(65) Prior Publication Data

US 2006/0091247 A1    May 4, 2006

(51) Int. Cl.
*B02C 25/00* (2006.01)
(52) U.S. Cl. .................... 241/36; 241/100; 241/236
(58) Field of Classification Search ............. 241/236, 241/100, 36
See application file for complete search history.

(56) References Cited

U.S. PATENT DOCUMENTS

| | | |
|---|---|---|
| 1,218,632 A | 3/1917 | Derry |
| 2,686,466 A | 8/1954 | Lee |
| 2,811,329 A | 10/1957 | Press et al. |
| 2,910,206 A | 10/1959 | Hodgson |
| 2,970,533 A | 2/1961 | Allen |
| 3,419,223 A | 12/1968 | Morin |
| 3,450,297 A | 6/1969 | Clerk |
| 3,682,402 A | 8/1972 | Goldhammer |
| 3,711,034 A | 1/1973 | Ehinger |
| 3,720,346 A | 3/1973 | Cypher |
| 3,724,766 A | 4/1973 | Bosland |
| 4,081,105 A | 3/1978 | Dagonnet et al. |
| 4,124,169 A | 11/1978 | Hatanaka |
| 4,172,400 A | 10/1979 | Brierley |
| 4,192,467 A | 3/1980 | Hatanaka |
| 4,564,146 A | 1/1986 | Bleasdale |
| 4,637,560 A | 1/1987 | Goldhammer |
| D299,035 S | 12/1988 | Nishibori et al. |

(Continued)

FOREIGN PATENT DOCUMENTS

CN    2638842    9/2004

(Continued)

OTHER PUBLICATIONS

Williams-Sonoma Catalog, Soft Touch Shredder/Trash Can, Williams-Sonama, Inc., Date: "Unknown".

(Continued)

*Primary Examiner*—Mark Rosenbaum
(74) *Attorney, Agent, or Firm*—Pillsbury Winthrop Shaw Pittman LLP

(57) ABSTRACT

A shredder is disclosed. The shredder includes a waste receptacle that has an interior waste receiving space, and a shredder mechanism that includes a motor and cutter elements. The shredder mechanism is positioned so that shredded articles are discharged downwardly into the waste receiving space. The receptacle includes a waste opening separate from the shredder mechanism for enabling articles to be discarded though the waste opening and received in the waste receiving space without passing through the shredder mechanism. A cover is moveable between a closed position that covers the waste opening, and an open position that opens the waste opening. A sensor for sensing the position of the cover is operatively connected to the shredder mechanism so that the shredder mechanism is inoperable at least when the sensor senses that the cover is in the open position. Other variations and improvements to shredders are also disclosed.

13 Claims, 12 Drawing Sheets

U.S. PATENT DOCUMENTS

| | | | |
|---|---|---|---|
| 4,817,877 A | 4/1989 | Itoh et al. | |
| 4,821,967 A | 4/1989 | Moriyama | |
| 4,842,205 A | 6/1989 | Araki et al. | |
| 4,893,722 A | 1/1990 | Jones | |
| 4,957,243 A | 9/1990 | Kanagaki et al. | |
| 4,973,004 A | 11/1990 | Krause et al. | |
| 5,035,366 A | 7/1991 | Hashimoto et al. | |
| 5,044,270 A | 9/1991 | Schwelling | |
| 5,163,574 A | 11/1992 | Sosan | |
| 5,190,183 A | 3/1993 | McNaughton et al. | |
| 5,195,649 A | 3/1993 | Wolters | |
| 5,246,119 A | 9/1993 | Heffner | |
| 5,249,693 A | 10/1993 | Gillispie et al. | |
| 5,269,473 A | 12/1993 | Strohmeyer et al. | |
| 5,320,241 A | 6/1994 | Evans | |
| 5,372,271 A | 12/1994 | Miller et al. | |
| 5,421,252 A | 6/1995 | Reichel | |
| D362,866 S | 10/1995 | Johansson | |
| 5,538,338 A | 7/1996 | Biggers | |
| D375,973 S | 11/1996 | Kennedy et al. | |
| 5,826,809 A | 10/1998 | Kroger | |
| 5,839,675 A | 11/1998 | Henreckson et al. | |
| 5,853,131 A | 12/1998 | Cheng | |
| D404,756 S | 1/1999 | Dziersk | |
| 5,897,065 A | 4/1999 | Schwelling | |
| D412,716 S | 8/1999 | Kroger | |
| 5,961,059 A | 10/1999 | Kroger | |
| 5,969,310 A | 10/1999 | Schwelling | |
| 5,988,542 A | 11/1999 | Henreckson et al. | |
| 6,010,024 A | 1/2000 | Wang | |
| 6,055,394 A | 4/2000 | Suda et al. | |
| 6,079,645 A | 6/2000 | Henreckson et al. | |
| 6,116,528 A | 9/2000 | Schwelling | |
| D434,433 S | 11/2000 | Hung | |
| D437,343 S | 2/2001 | Ho | |
| 6,193,091 B1 | 2/2001 | Olivetti | |
| 6,274,828 B1 | 8/2001 | Chu | |
| 6,276,553 B1 | 8/2001 | Vulcano | |
| D451,948 S | 12/2001 | Wu et al. | |
| D454,907 S | 3/2002 | Ho | |
| D455,170 S | 4/2002 | Ho | |
| 6,378,721 B1 | 4/2002 | Williams | |
| 6,460,790 B1 | 10/2002 | Wu Huang | |
| D474,231 S | 5/2003 | Lammers et al. | |
| 6,595,444 B2 | 7/2003 | Schwelling | |
| 6,626,316 B2 | 9/2003 | Yang | |
| D481,416 S | 10/2003 | Chang | |
| 6,672,575 B2 | 1/2004 | Flower et al. | |
| 6,708,607 B1 | 3/2004 | Schwelling | |
| 6,962,301 B1 | 11/2005 | Chang | |
| 6,964,386 B2 | 11/2005 | Ho | |
| 2003/0006330 A1 | 1/2003 | Chang | |
| 2003/0201267 A1 | 10/2003 | Yang et al. | |
| 2004/0028572 A1 | 2/2004 | Sham et al. | |
| 2005/0072869 A1 | 4/2005 | Ting | |
| 2005/0253004 A1 | 11/2005 | Hsieh et al. | |

FOREIGN PATENT DOCUMENTS

| | | |
|---|---|---|
| DE | 36 07 752 | 9/1987 |
| DE | 86 19 856 | 9/1988 |
| DE | 90 14 543 | 1/1991 |
| DE | 296 04 761 U1 | 5/1996 |
| DE | 296 22 139 | 4/1997 |
| DE | 196 18 478 | 9/1997 |
| DE | 100 23 284 | 11/2001 |
| DE | 20 2004 009 399 | 8/2004 |
| EP | 1 195 202 | 4/2002 |
| GB | 2 414 942 | 12/2005 |
| WO | 2005/097329 | 10/2005 |

OTHER PUBLICATIONS

PCT Partial International Search Report issued on International Application No. PCT/US2005/035567 dated Jan. 5, 2006.

Review of Royal RS9512C Shredder from internet website www.epinions.com.

International Search Report issued in PCT/US2005/035567 dated Apr. 24, 2006.

Written Opinion of the International Searching Authority issued in PCT/US2005/035567.

SHREDDER WITH SEPARATE WASTE OPENING

BACKGROUND OF THE INVENTION

1. Field of the Invention

The present invention relates generally to shredders. More particularly, the present invention relates to shredders that have separate waste openings.

2. Description of Related Art

Shredders for home and office use are becoming increasingly popular as a result of concerns of identity theft and security of proprietary information. Shredders can range in size from small personal units that may be placed on top of a waste container, as shown for example in U.S. Pat. No. 5,988,542, to large industrial-sized shredders that handle a very large volume of debris, as shown for example in U.S. Pat. No. 5,044,270. The shredders that are designed for personal use are typically associated with a waste container that is dedicated to collect the shredded material.

In general, the present application endeavors to provide various improvements over known shredders.

BRIEF SUMMARY OF THE INVENTION

One aspect of the invention relates to a shredder with a separate waste opening wherein the shredder mechanism is inoperable when the waste opening's cover is opened. In this aspect, the shredder includes a waste receptacle that has an interior waste receiving space, and a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The receptacle includes a waste opening that is separate from the shredder mechanism for enabling articles to be discarded through the waste opening and received in the waste receiving space without passing through the shredder mechanism. The shredder also includes a cover that is moveable between (1) a closed position that covers the waste opening, and (2) an open position that opens the waste opening, and a sensor for sensing the position of the cover operatively connected to the shredder mechanism. The shredder mechanism is inoperable at least when the sensor senses that the cover is in the open position.

Another aspect of the invention relates to a shredder with a separate waste opening wherein the shredder mechanism is inoperable when an article is entering the opening. In this aspect of the invention, the shredder includes a waste receptacle that has an interior waste receiving space, and a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The receptacle includes a waste opening that is separate from the shredder mechanism for enabling articles to be discarded through the waste opening and received in the waste receiving space without passing through the shredder mechanism. The shredder also includes a sensor for sensing an article entering the waste opening. The sensor is operatively connected to the shredder mechanism, and the shredder mechanism is inoperable at least when the sensor senses the article entering the waste opening.

A further aspect of the invention relates to an improved construction for emptying the waste container. In this aspect of the invention, the shredder includes a waste receptacle that has an exterior peripheral wall extending generally vertically and an interior waste receiving space, and a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The waste receptacle has a base frame and a removable waste container that provides the waste receiving space and at least a portion of the exterior peripheral wall. The base frame includes an upper portion on which the shredder mechanism is supported. The waste container is removably mounted beneath the upper portion to enable shredded articles from the shredder mechanism to be received in the waste receiving space. The removable mounting of the waste container enables the waste container to be removed from the base out from underneath the upper wall for emptying. The shredder also includes a sensor for sensing the position of the removable waste container to the shredder mechanism. The shredder mechanism is inoperable at least when the sensor senses that the removable waste container is removed.

Yet a further aspect of the invention relates to a shredder with a foot-operated cover. In this aspect of the invention, the shredder includes a waste receptacle that has an interior waste receiving space and a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The shredder also includes a cover that is moveable between (1) a closed position, and (2) an open position, and a foot pedal that is disposed at a bottom portion if the receptacle and operatively connected to the cover. The foot pedal is constructed and arranged to be actuated by a person's foot such that actuation of the foot pedal causes the cover to move to the open position.

Yet another aspect of the invention relates to a shredder with improved odor management. In this aspect of the invention, the shredder includes a waste receptacle that has an interior waste receiving space, and a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The receptacle includes a waste opening that is separate from the shredder mechanism for enabling articles to be discarded through the waste opening and received in the waste receiving space without passing through the shredder mechanism. The shredder also includes a electrically-powered air freshener.

Another aspect of the invention relates to a shredder with a separate waste opening wherein the shredder is protected when an article is entering the opening. In this aspect of the invention, the shredder includes a waste receptacle having an interior waste receiving space, and a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The receptacle includes a waste opening separate from the shredder mechanism for enabling articles to be discarded through the waste opening and received in the waste receiving space without passing through the shredder mechanism. A door is configured to prevent the articles being discarded through the waste opening from contacting the cutter elements. The door is biased in a closed position so that the waste opening is closed and configured to be pushed to an open position so that the articles may enter the waste opening.

A further aspect of the invention relates to a shredder with a tilt-out waste receptacle. In this aspect of the invention, the shredder includes a housing, and a waste receptacle that is received by the housing. The waste receptacle defines an interior waste receiving space. The shredder also includes a shredder mechanism that includes a motor and cutter elements. The shredder mechanism enables articles to be shredded to be fed into the cutter elements and the motor is operable to drive the cutter elements so that the cutter elements shred the articles therein. The shredder mechanism is positioned so that the shredded articles are discharged into the waste receiving space. The receptacle is pivotable relative to the housing to define (a) a closed position and (b) an open position. The open position allows a person to dispose of an object through a waste opening between a sidewall of the waste receptacle and the housing, without passing the object through the shredder mechanism. The shredder also includes a sensor for sensing the position of the waste receptacle and operatively connected to the shredder mechanism. The shredder mechanism is inoperable when the sensor senses that the waste receptacle is in the open position.

These and other aspects of the invention will become apparent from the following detailed description when taken in conjunction with the accompanying drawings, which are part of this disclosure and which illustrate, by way of example, the principles of this invention.

BRIEF DESCRIPTION OF THE DRAWINGS

Features of the invention are shown in the drawings, in which like reference numerals designate like elements. The drawings form part of this original disclosure, in which.

DETAILED DESCRIPTION OF EMBODIMENTS OF THE INVENTION

Figure 1:
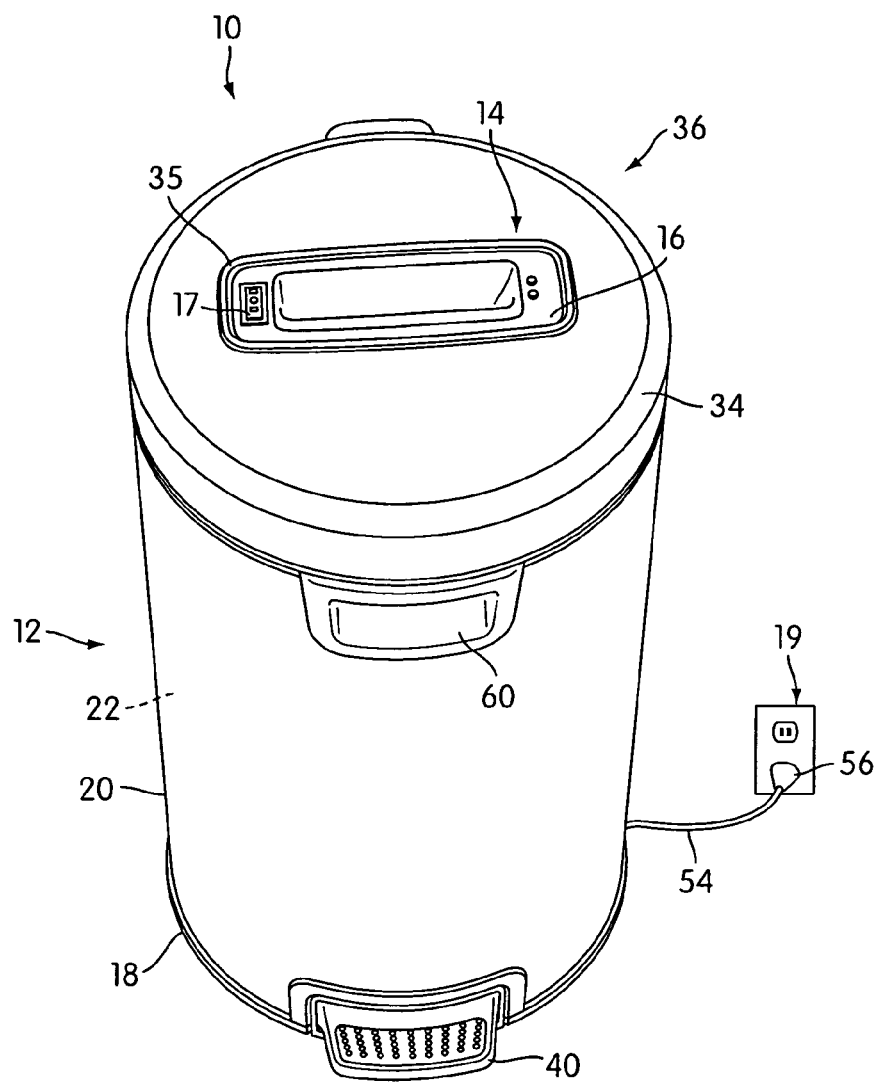
FIG. 1 is a top perspective view of an embodiment of a shredder of the present invention, with a cover in a closed position.

FIG. 1 shows an embodiment of a shredder 10. The shredder 10 includes a waste receptacle 12 that is suitable for receiving waste materials and objects, and a shredder mechanism 14 that is supported by or otherwise located above the waste receptacle 12. The waste receptacle 12 may have any construction or configuration, and in the illustrated embodiment includes a bottom portion 18 and a sidewall 20 that extends upward from the bottom portion 18. As shown, the bottom portion 18 is substantially circular in shape, but it is understood that this is but one of a variety of possible shapes. For example, the bottom portion 18 may be square, rectangular, polygonal, etc. The bottom portion 18 is preferably substantially flat, at least on its bottom side, so that the entire waste receptacle 12 is stable when placed on a floor or ground. Of course, wheels, legs, or other features may be attached to the bottom side of the bottom portion 18 and still be within the contemplated scope of the invention. The bottom portion 18 may be manufactured from metal, plastic, or any other material that is commonly used in the manufacturing of waste containers.

The sidewall 20 extends upward from the bottom portion 18 such that it defines and substantially surrounds an interior waste receiving space 22 of the waste receptacle 12. As shown, the sidewall 20 is shaped substantially as a cylinder, but it is understood that the sidewall may be any shape, but is preferably complementary to the shape of the bottom portion 18. Thus, if the bottom portion 18 is rectangular in shape, the interior 22 that is created by the sidewall 20 is preferably substantially rectangular in cross-section. The sidewall 20 may be one continuous piece of material, or may be sectioned, as will be discussed in further detail below. Like the bottom portion 18, the sidewall 20 is preferably manufactured from metal, plastic or any other material that is commonly used to manufacture waste containers. In embodiments in which the shredder mechanism 14 is supported by the sidewall 20 of the waste receptacle, the thickness of the sidewall 20 should be adequate to support the weight of the shredder mechanism 14 without allowing the sidewall 20 to buckle or otherwise distort.

Figure 2:
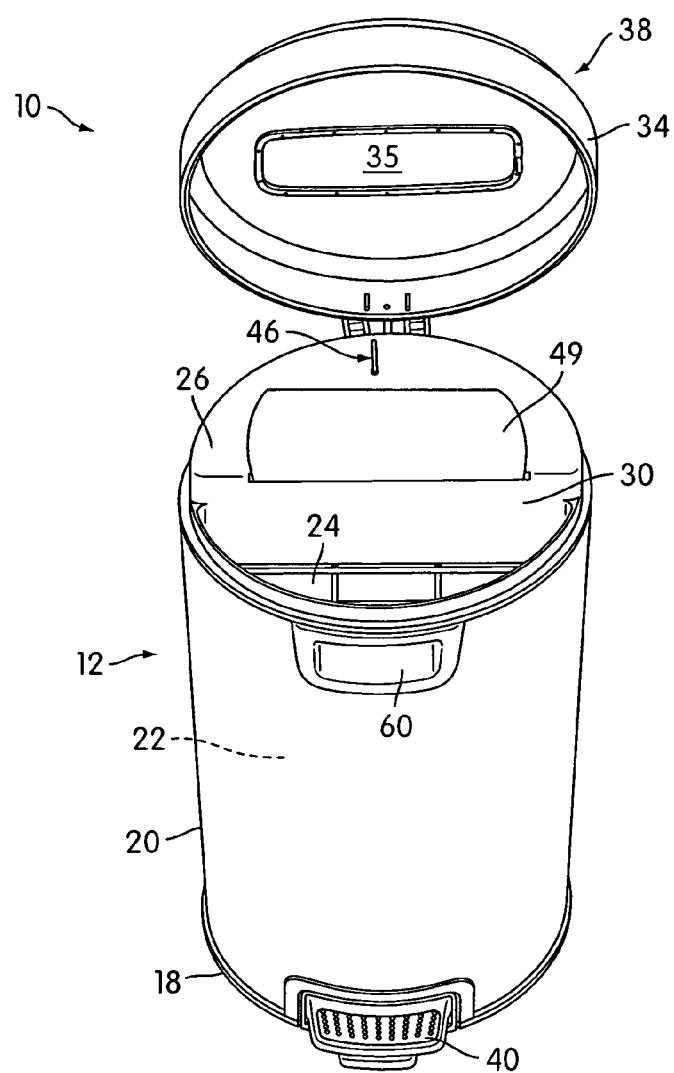
FIG. 2 is a top perspective view of the shredder of FIG. 1, with the cover in an open position.

As shown in FIG. 2, the shredder mechanism 14 is supported by the sidewall 20 of the waste receptacle 12 and a separate waste opening 24 is created between the shredder mechanism 14 and a portion of the sidewall 20. As shown, the waste opening 24 is adjacent the shredder mechanism 14. The opening 24 is considered to be separate from the shredder mechanism 14 because materials may enter the waste receptacle 12 either through the shredder mechanism 14 or the waste opening 24. Thus, an opening could be bounded on one side by parts of the shredder mechanism 14, and would be considered separate so long as articles could pass through it separately without also passing through the shredder mechanism 14. Other arrangements are contemplated and are considered to be within the scope of the invention.

Preferably, the waste opening 24 is at least one-fourth of the cross-sectional area of the interior 22 of the waste receptacle 12. More preferably, the waste opening 24 is at least one-third of the cross-sectional area of the interior 22 of the waste receptacle 12. In other words, the waste opening 24 should be large enough to receive waste items of a reasonable size, without causing undo burden to a person inserting the waste into the waste receptacle 12. However, the waste opening 24 may have any size or configuration and is not limited to the examples described or specified herein.

As shown in FIG. 2, the shredder 10 further includes an upper portion 26 that is preferably complementary in shape to the sidewall 20. The upper portion 26 may be a molded piece of plastic material that includes a shredder-receiving portion 28 and the waste opening 24. This way, internal walls 30 may be included, at the waste opening 24 in particular, to help separate the shredder mechanism 14 from the waste opening 24 below the top surface of the waste receptacle 12. The internal walls 30 may be arranged to create a chute-like structure that may assist in directing objects that enter the waste opening 24 into the interior 22 of the waste receptacle 12. As an optional feature, the upper portion 26 may be removable from the waste receptacle 12 so that the interior 22 of the waste receptacle 12 may be more easily accessed. Such a configuration would help in the removal of the waste from the waste receptacle 12 when the capacity of the waste receptacle 12 is reached.

Figure 3:
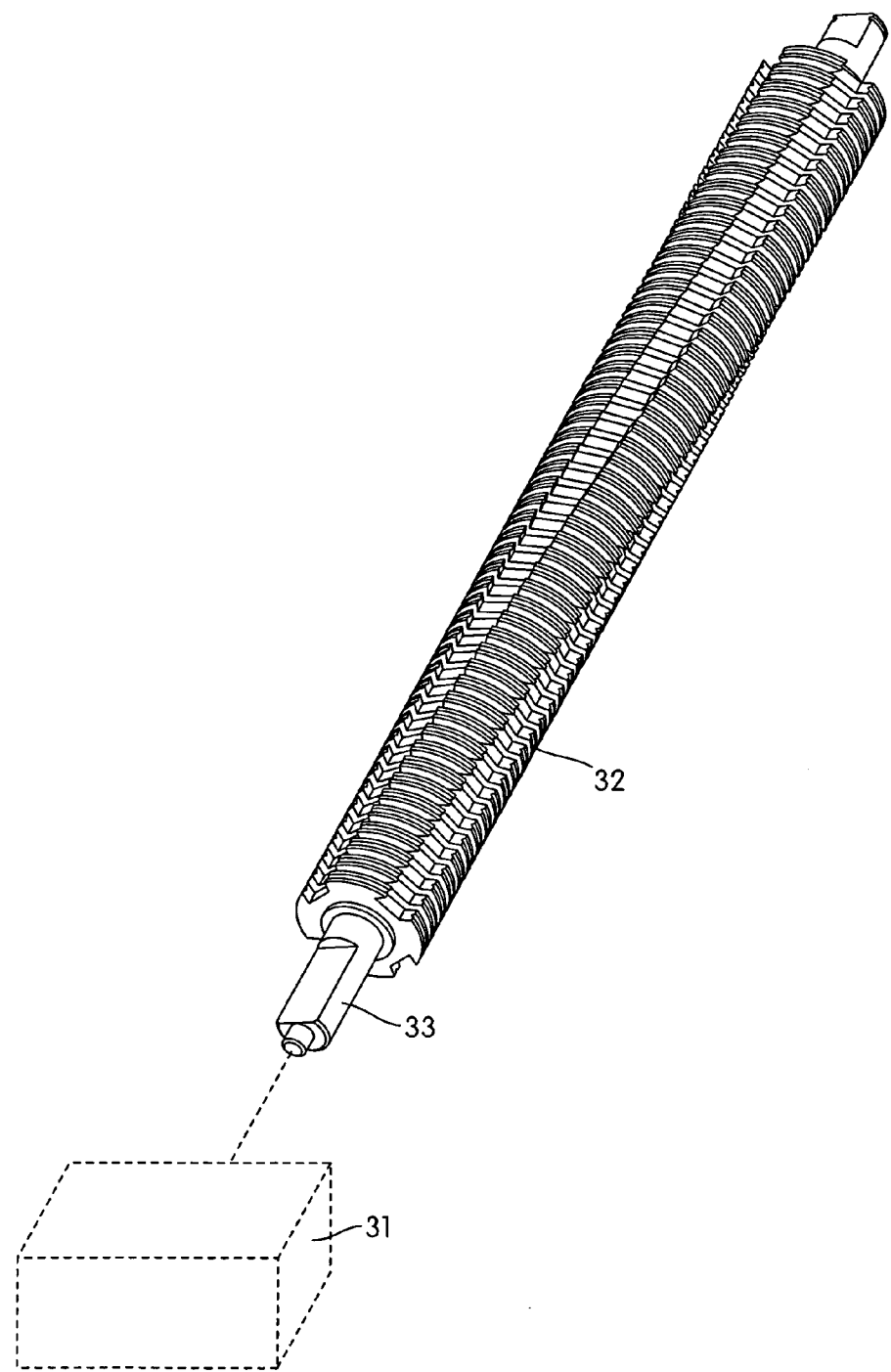
FIG. 3 is a perspective view of an internal portion of a shredder mechanism of the shredder of FIG. 1.

The shredder mechanism 14 includes a motor 31 and a plurality of cutter elements 32 that are disposed within a shredder housing 16. The cutter elements 32 are mounted on a pair of parallel rotating shafts 33, one of which is shown in FIG. 3. The motor 31 operates using electrical power to rotatably drive the shafts 33 and the cutter elements 32 through a conventional transmission (not shown) so that the cutter elements 32 shred articles fed therein. The shredder mechanism 14 may also include a sub-frame for mounting the shafts 33, the motor 31 and the transmission. The operation and construction of such a shredder mechanism 14 are well known and need not be described herein in detail.

The shredder mechanism 14 preferably includes a switch 17 that connects the motor 31 to a power supply 19. Typically, the power supply 19 will be connected to the shredder 10 via a standard power cord 54 with a plug 56 on its end that plugs into a standard AC outlet, as shown in FIG. 1. The switch 17 is configured to allow the user to choose an operational mode. A typical switch 17 includes a plurality of positions, including but not limited to an off position, a forward position, a reverse position, an automatic position, or any combination thereof. When the switch 17 is in the off position, the shredder mechanism 14 is inoperable, as no electrical power signal is supplied to drive the motor 31. When the switch 17 is in the forward position, the motor 31 is energized and operating to rotate the shafts 33 and cutter elements 32, even if no material is in the shredder mechanism 14. In the forward position, material is moved through the shredder mechanism 14 and discharged from the outlet of the shredder mechanism 14 and into the waste receptacle 12. When the switch 17 is in the reverse position, the motor 31 is driven by a power signal of reverse polarity and the direction of rotation of the shafts 33 and cutter elements 32 is reversed. Thus, the material is fed back towards the inlet of the shredder mechanism 14 and away from the outlet of the shredder mechanism 14. The reverse position is commonly used to clear jams. When the switch 17 is in the automatic position, a sensor (e.g., an optical sensor) within or adjacent to the shredder mechanism 14 is used to determine whether material has entered or is being fed into the shredder mechanism 14. Upon such sensing, the motor 31 is turned on, and the shredder mechanism 14 operates as described above with respect to the forward position until the materials are discharged therefrom. Generally, the construction and operation of the switch 17 for controlling the motor 31 are well known and any construction for such a switch 17 may be used.

In the embodiment illustrated in FIGS. 1 and 2, a cover 34 is configured to cover at least the waste opening 24. The cover 34 may be hingedly connected to the sidewall 20, although it is contemplated that the cover 34 may be fully removable from the sidewall 20 as well. The cover 34 is moveable between a closed position 36 and an open position 38. When the cover 34 is in the closed position 36, as shown in FIG. 1, the cover 34 covers the waste opening 24 such that no waste can enter the waste receptacle 12 through the waste opening 24. However, in the embodiment shown in FIG. 1, when the cover 34 is in the closed position 36, the shredder mechanism 14 is still accessible through an opening 35 in the cover 34 so that material can still be fed into the shredder mechanism 14. The opening 35 in the cover 34 is preferably large enough to allow access to the switch 17 on the shredder mechanism 14 as well. This way, the shredder mechanism 14 is fully functional, even when the cover 34 is in the closed position 36. If a larger item of waste, or non-shreddable material, needs to be disposed of, the user can simply move the cover 34 to the open position 38, as shown in FIG. 2, and dispose of the item through the waste opening 24. It is understood that the open position 38 is defined to include all positions of the cover 34 besides the closed position 36. Thus, the open position 38 is contemplated to include the intermediate positions of the cover 34 between the closed position 36 and the fully open position 38 that is shown in FIG. 2. After objects have been placed in the waste receptacle 12 via the waste opening 24, the cover 34 can be returned to the closed position 36, thereby concealing the contents of the waste receptacle 12 once again. This way, if food waste has been deposited into the waste receptacle 12, any odor emanating therefrom will be significantly contained.

The cover 34 may have any construction or configuration and the illustrated one is not intended to be limiting. For example, the cover 34 may also be designed to cover the shredder mechanism 14 so that when the cover 34 is in the closed position 36, neither the shredder mechanism 14 nor the waste opening 24 is accessible. Further, for certain aspects of the invention, the cover 34 is an optional feature, and thus may be omitted.

Figure 4:
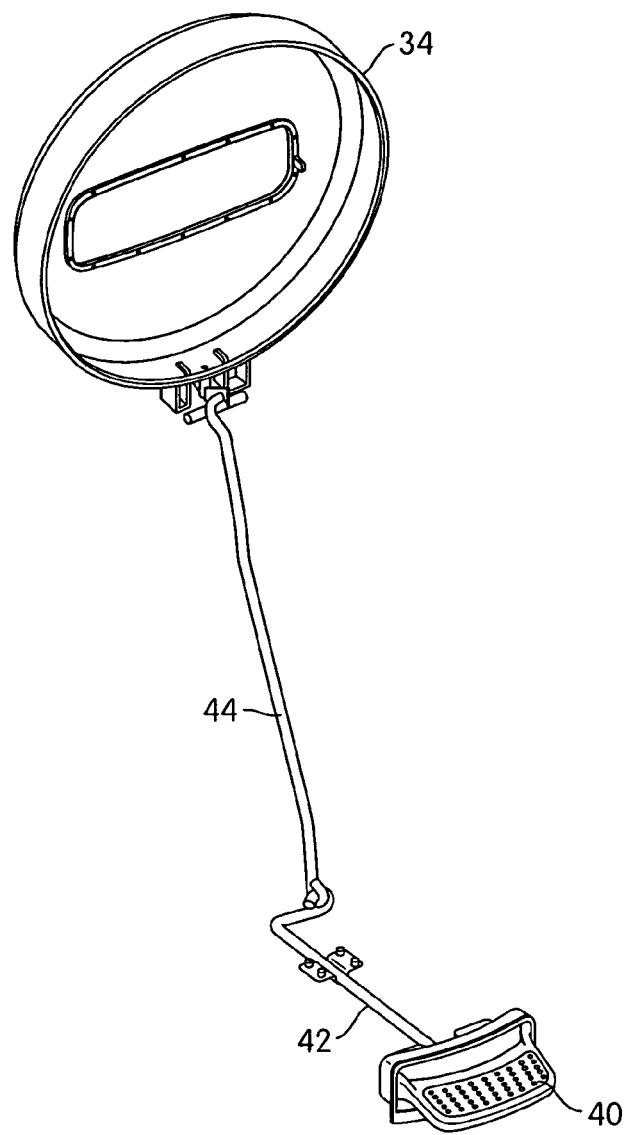
FIG. 4 is a bottom perspective view of a foot pedal assembly and the cover of the shredder of FIG. 1.

As shown in FIGS. 1 and 2, a foot pedal 40 is disposed at a lower portion of the shredder 10 such that it is in the vicinity of the bottom portion 18 of the waste receptacle 12. The foot pedal 40 is designed to receive a person's foot and is operatively connected to the cover 34 so that a person can open the shredder 10 and access the waste receptacle 12 without the use of hands. Preferably, the foot pedal 40 is operatively connected to the cover 34 with a first link 42 and a second link 44, as shown in FIG. 4. As shown, the first link 42 is operatively connected to the foot pedal 40 at one end, and the second link 44 at the opposite end. The first link 42 is substantially horizontal when the shredder 10 is in its normal orientation, and is supported by the underside of the bottom portion 18 of the waste receptacle 12. The second link 44 is substantially vertical when the shredder 10 is in its normal orientation, and is preferably located within the sidewall 20 of the waste receptacle 12. It is understood that the first and second links 42, 44 may be disposed on the exterior of the waste receptacle 12, the interior 22 of the waste receptacle 12, or within the bottom portion 18 or sidewall 20 of the waste receptacle 12, respectively.

The first link 42 is connected to the second link 44 so that when the first link 42 is caused to move in one direction upon actuation of the foot pedal 40, the second link 44 moves downward, thereby causing the cover 34 to move to the open position 38. This movement is created by the location of the hinge of the cover 34 and the connection point of the second link 44 to the cover 34, as would be appreciated by one of skill in the art. The weight of the cover 34 and location of the hinge allow the cover 34 to return to the closed position 36 once the applied force to the foot pedal 40 is removed. Thus, upon removal of the force from the foot pedal 40, gravity allows the cover 34 to return to the closed position 36, which causes the second link 44 to move upward, which causes the first link 42 to move towards the second link 44, and the foot pedal 40 to return to its upwardly biased position. The use of the foot-operated actuation of the cover 34 is merely optional and various aspects of the invention may be practiced without it. Additionally, even in those constructions where it is used, other constructions may be used besides the one illustrated herein.

Figure 5A:
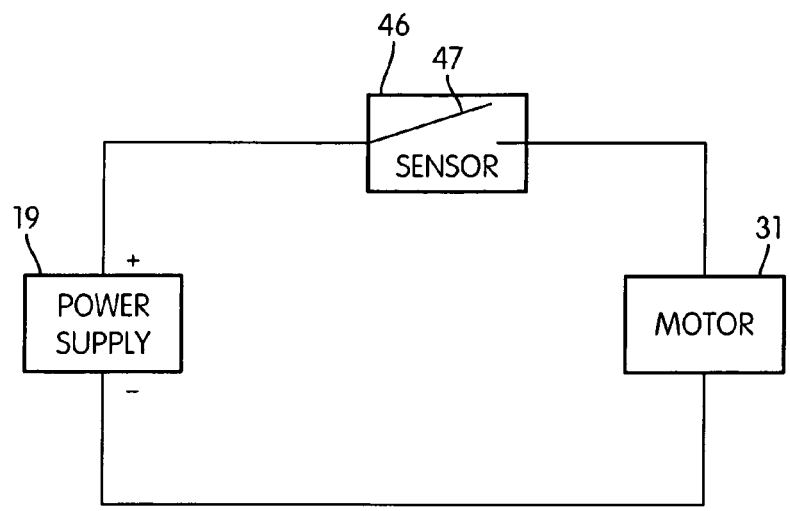
FIG. 5a is a circuit diagram showing an embodiment of a sensor connected to the shredder mechanism of FIG. 1, when the shredder mechanism is inoperable.
Figure 5B:
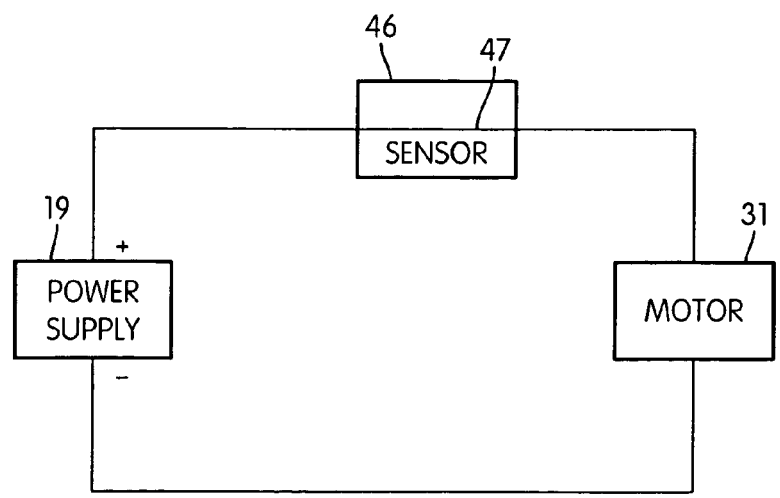
FIG. 5b is a circuit diagram showing the embodiment of the sensor connected to the shredder mechanism of FIG. 5a, when the shedder mechanism is operable.

Returning to FIG. 2, the shredder 10 may also include a sensor 46 that is operatively connected to the cover 34 in such a way that the sensor 46 may sense the position of the cover 34, such as by a mechanical or contact switch, an optical device, or by any other mechanism. The sensor 46 is also operatively connected to the shredder mechanism 14. When the sensor 46 senses that the cover 34 is in the closed position 36, the shredder mechanism 14 is fully operational. However, when the sensor 46 senses that the cover 34 is in the open position 38, or has moved from the closed position 36, the shredder mechanism 14 becomes inoperable. Specifically, the sensor 46 will disable power to the shredder motor 31 when the cover 34 is in the open position 38. For example, when the cover 34 is opened, the sensor 46 may responsively open a switch 47 between the motor 31 and the power supply 19, thereby discontinuing the delivery of the power signal to the motor 31, as shown in FIG. 5a. As a result of this sensor feature, when objects are entering the waste receptacle 12 through the waste opening 24, the shredder mechanism 14 cannot operate. When the cover 34 returns to the closed position 36, the sensor 46 may responsively close the switch 47, thereby allowing the power supply 19 to deliver power to the motor, as shown in FIG. 5b. In various aspects of the invention, the sensor 46 may be optional, and may be omitted. Further, even when a sensor 46 is used, its construction is not limited to that described or illustrated herein and any suitable sensor may be used.

The sensor 46 may also be operatively connected to a shield 49 that is constructed and arranged to cover the shredder mechanism 14 when the cover 34 is in the open position 38. This way, when the cover 34 is in the open position 38, the shredder mechanism 14 may be protected from liquids and any other items that may damage the shredder mechanism 14. The shield 49 may be mechanically actuated such that displacement of an arm 51 of the sensor 46 may move the shield 49 by moving one or more mechanical links (not shown), or that shield 49 may be powered so that when the sensor 46 senses that the cover 34 is in the open position 38, power is routed to the shield 49 to move it in the position shown in FIG. 2. The shield 49 should be considered to be optional, and may be used in addition to the cover 34, as shown, may be used without the cover 34, or may not be used at all. The illustrated embodiment is not intended to be limiting in any way.

Figure 6A:
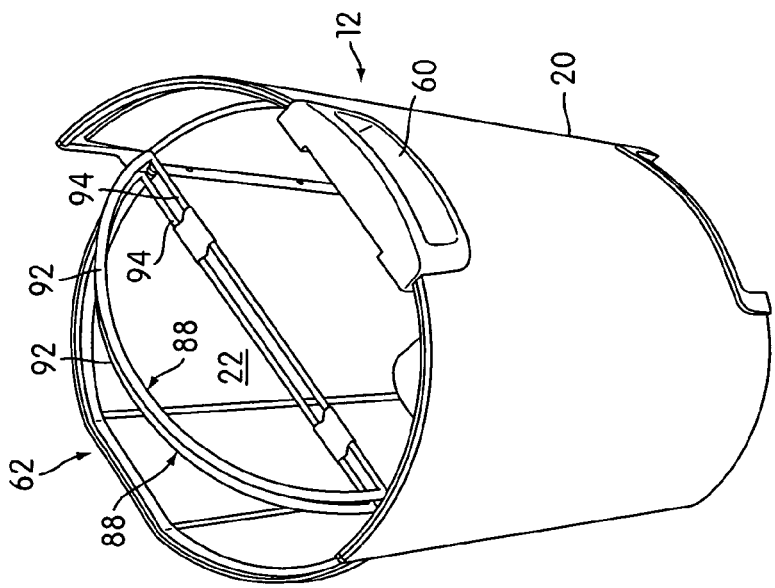
FIG. 6a is a top perspective view of a portion of a sidewall separated from the shredder of FIG. 2.
Figure 6B:
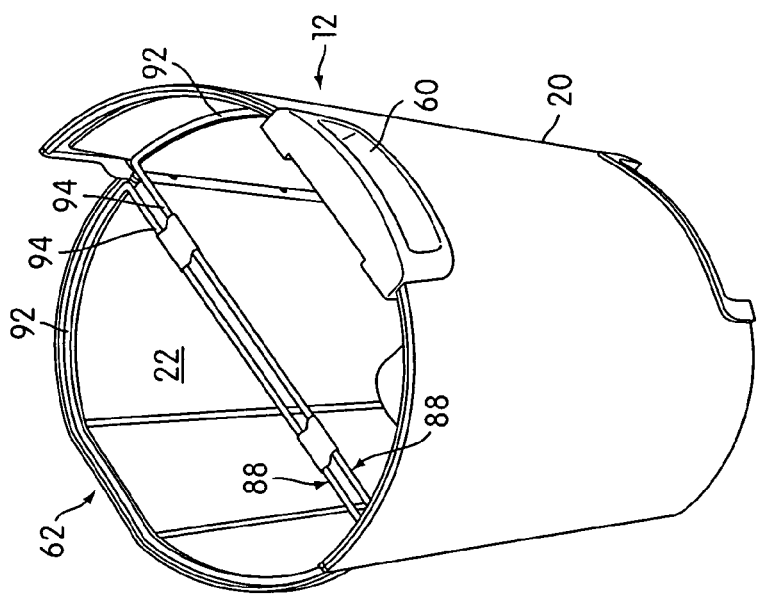
FIG. 6b is a top perspective view of the portion of the sidewall of FIG. 6a with a frame in a partially removed position.
Figure 7:
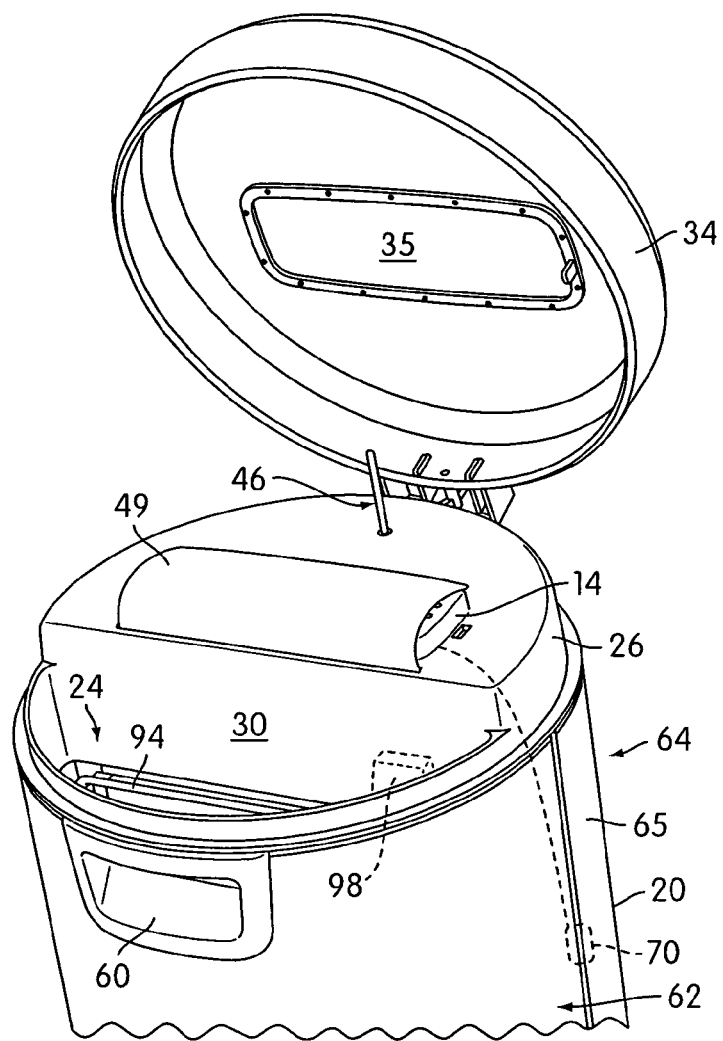
FIG. 7 is more detailed top perspective view of the shredder of FIG. 2.

As shown in FIGS. 6a, 6b, and 7, a handle 60 that is suitable for receiving a person's hand may be provided on an exterior part of an exterior peripheral wall of the receptacle 12 (i.e. the generally vertically extending sidewall 20). A removable waste container 62 is also provided. The waste container 62 provides the waste receiving space 22 and the portion of the wall on which the handle 60 is located. As shown, the waste receptacle 12 includes a base frame 64 that includes the upper portion 26, the bottom portion 18, and a stationary part 65 of the sidewall 20. The base frame 64, however, may have any construction and is not limited to that illustrated or described. The waste container 62 is removably mounted beneath the upper portion 26 to enable shredded articles from the shredder mechanism 14 or articles discarded through the waste opening 24 to be received in the waste receiving space 22. The removable mounting of the waste container 62 enables the waste container 62 to be easily removed from the base frame 64 out from underneath the upper portion 26 by pulling on the handle 60 for emptying. This is beneficial because it avoids the need for moving or handling the shredder mechanism 14. Further, having the handle 60 on the removable section of the sidewall 20 and enabling that section to be removed as part of the waste container 62 is beneficial because it avoids the need for a door to conceal the waste container 62, or having the waste container 62 exposed.

Preferably, a sensor 70 is provided that can sense when the waste container 62 is removed. The sensor 70 may be a mechanical or contact switch, an optical device, or any other mechanism. The sensor 70 is operatively connected to the shredder mechanism 14 so that the shredder mechanism 14 is inoperable upon such sensing. This may be done by discontinuing delivery of the power signal to the motor 31, such as is described above with respect to the sensor 46 for the cover 34, or in any other manner. This way, if the waste container 62 is removed even when the cover 34 is in the closed position 36, the shredder mechanism 14 will not operate.

Figure 8:
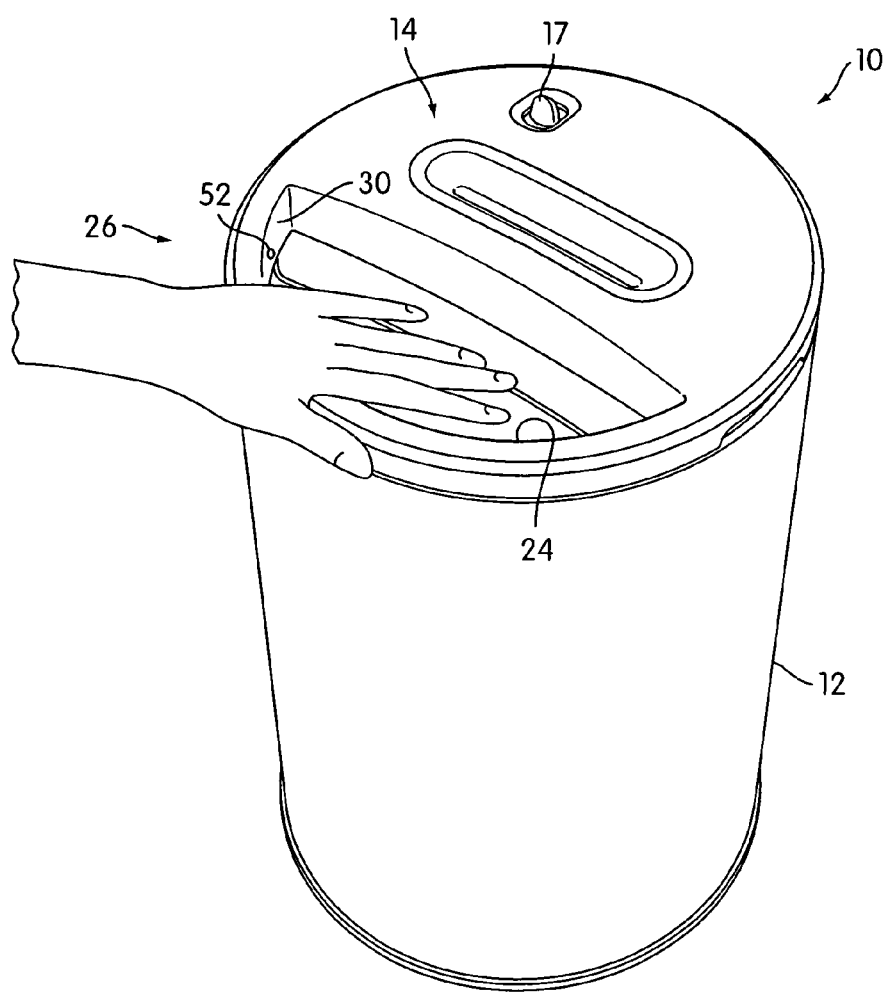
FIG. 8 is a top perspective view of an embodiment of a shredder of the present invention.

As shown in FIG. 8, as an alternative or supplement to sensing movement of the cover 34 to the open position 38, a sensor 52 may be disposed such that it can sense when an object is entering the waste opening 24, and communicate such sensing so that the shredder mechanism 14 becomes inoperable in essentially the same manner as described above for the sensor 46 that is operatively connected to the cover 34. FIG. 5b shows a how the sensor 52 interacts with the shredder mechanism 14. The sensor 52 is preferably disposed within the waste opening 24 itself, such as in the walls 30 of the upper portion 26, or the sidewall 20 of the waste receptacle 12, or any other configuration, so long as the sensor 52 can sense when the object is entering the waste opening 24. The sensor 52 is an infra-red (IR) sensor that senses heat radiated from any object entering the waste opening 24, or an optical sensor, or any other mechanism that can sense an object entering the waste opening 24. Upon sensing the object entering the waste opening 24, power to the motor 31 of the shredder mechanism 14 will be disabled. The sensor 52 may be used in combination with or instead of the sensor 46 that senses the position of the cover 34. The use of such a sensor may allow the shredder 10 to be constructed without a cover 34.

Figure 9:
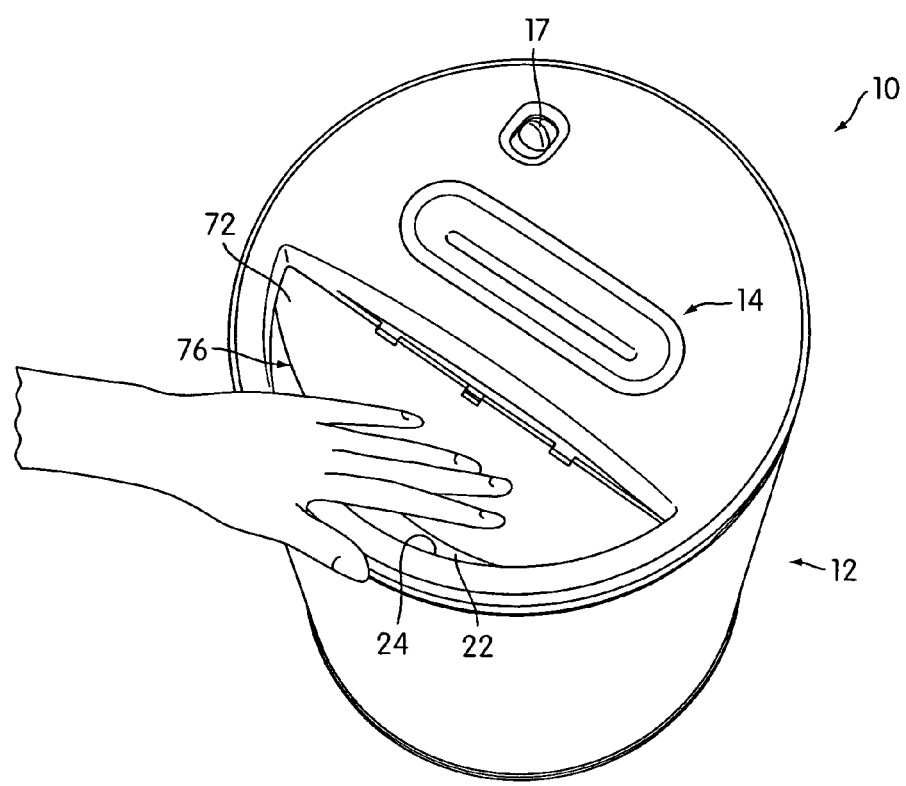
FIG. 9 is a top perspective view of an embodiment of a shredder of the present invention.

As shown in FIG. 9, as an alternative or supplement to the cover 34 and/or sensor 52, a door 72 may be provided to physically close off the waste opening 24 when in a closed position, and open the waste opening 24 when in an open position 76. The door 72 may be mounted so that it is biased in the closed position, and movable to the open position 76 by pushing the door 72 with an object. The door 72 may be configured to protect the shredder mechanism 14 when in the open position 76, thereby preventing objects from contacting the cutter elements 32. In the illustrated embodiment, the door 72 is a flap-type door that is rotatably mounted at one end at the side of the waste opening 24 closest to the shredder mechanism 14. With this configuration, when the door 72 is pushed open, the door 72 will rotate into the interior 22 of the waste receptacle 12 such that it creates an interior shield for the shredder mechanism 14. This way, as objects enter the waste opening 24, they will not contact the shredder mechanism 14.

Figure 10:
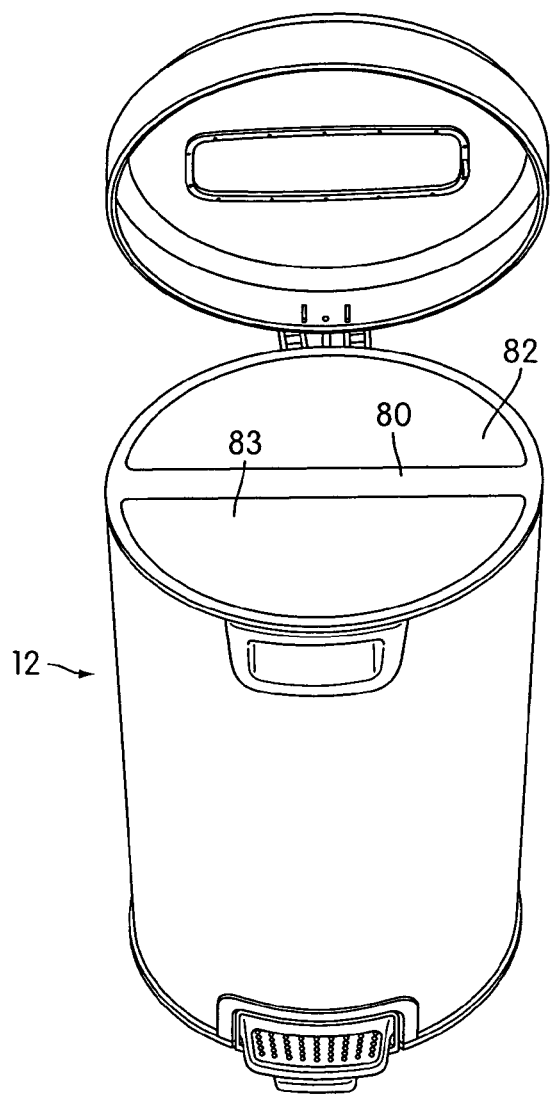
FIG. 10 is a top perspective view of an interior of a shredder of the present invention.

As shown in FIG. 10, in which the shredder mechanism 14 has been removed for clarity, the waste receptacle 12 may also include at least one interior wall 80 that extends upward from the bottom portion 18 so as to create at least two compartments 82, 83 within the waste receptacle 12. It is understood that at least one interior wall 80 may be provided in the removable waste container 62 in a similar fashion. Preferably, the interior wall 80 is arranged so that one compartment 82 receives the shredded material that has passed through the shredder mechanism 14, and another compartment 83 receives the objects that have entered the waste opening 24 of the waste receptacle 12. The compartments 82, 83 may be separately lined with, for example, trash bags. This way, the compartments 82, 83 may be more easily emptied, as needed. Specifically, if the articles discarded through the opening 24 are not paper products that can be recycled, the separated shredded paper, which is typically recyclable, may be sent for recycling, and the mixed trash received in the other compartment may be discarded as regular trash.

Alternatively, the shredder 10 may also include at least one frame 88, as shown in FIGS. 6a and 6b, that is operatively connected to the sidewall 20. It is also contemplated that the frame 88 may be operatively connected to the upper portion 26 in embodiments that include the upper portion 26. As shown in FIGS. 6a and 6a, the frame 88 is constructed and arranged to support at least one flexible liner (not shown), such as a trash bag. Preferably, two frames 88 are used to support two flexible liners, one to receive shredded materials that have passed through the shredder mechanism 14, and one to receive objects that have passed through the waste opening 24 and into the interior 22 of the waste receptacle 12, although it is understood that only one frame 88 may be used. As shown, the frame 88 includes an outer rim 92 that is complementary in shape to the interior shape of the sidewall 20, and a substantially straight member 94 that is connected to opposite end of the outer rim 92, as shown in FIGS. 6a and 6b. Of course, the entire frame 88 may be of a one-piece construction, or may include the two pieces 92, 94 that are physically connected to each other. As shown, the frame 88 connects to an upper portion of the sidewall 20 with the flexible liner held therebetween. Each frame 88 may pivot about its substantially straight member 94, as shown in FIG. 6b, such that the our rim 92 may be pulled away from the sidewall 20, thereby releasing the flexible liner. By using two frames 88, an internal wall to the waste receptacle 12 itself does not need to be provided because the shredded material may be kept separate from the non-shredded material.

Returning to FIG. 7, an electrically-powered air freshener 98 that includes a diffusible aromatic element and an electrically-powered fan and/or heater for facilitating diffusion of the aromatic element may also be provided. A powered or non-powered charcoal filtration system may also be used as part of or in addition to the air freshener 98. In one embodiment, the air freshener 98 is mounted to the interior 22 of the shredder 10 so that it is in fluid communication with the interior 22 of the waste receptacle 12 and the waste disposed therein. Such fluid communication provides additional odor control. Preferably, the air freshener 98 is powered by the same power source 26 that powers the shredder mechanism 14.

Figure 11:
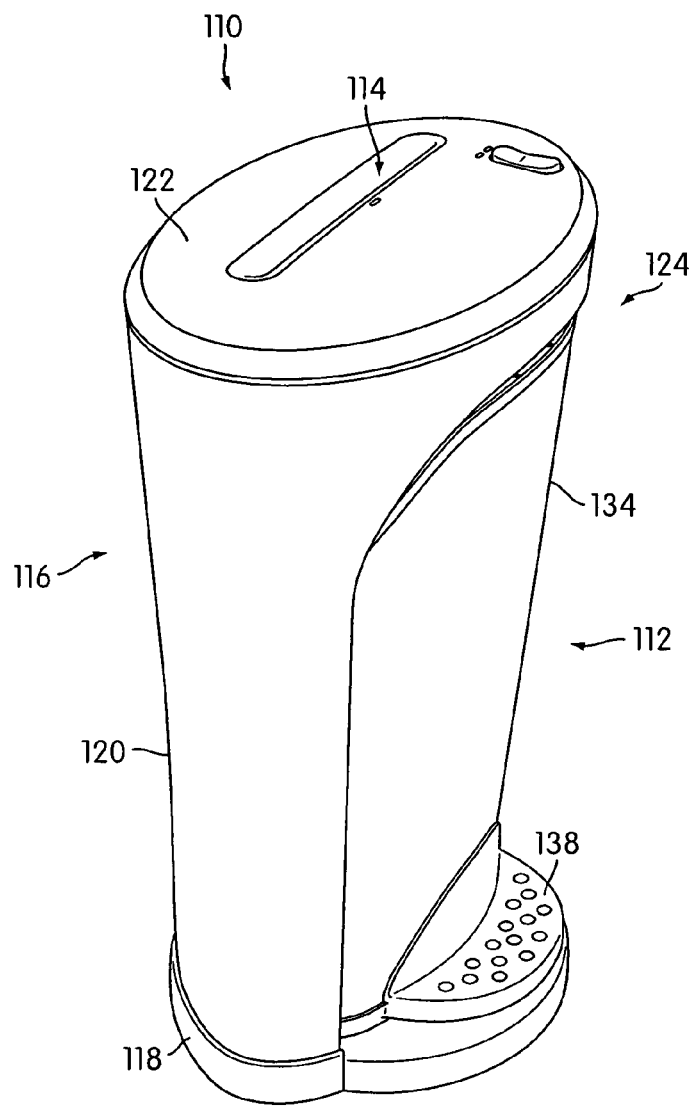
FIG. 11 is a top perspective view of an embodiment of a shredder of the present invention, with a waste receptacle in a closed position.
Figure 12:
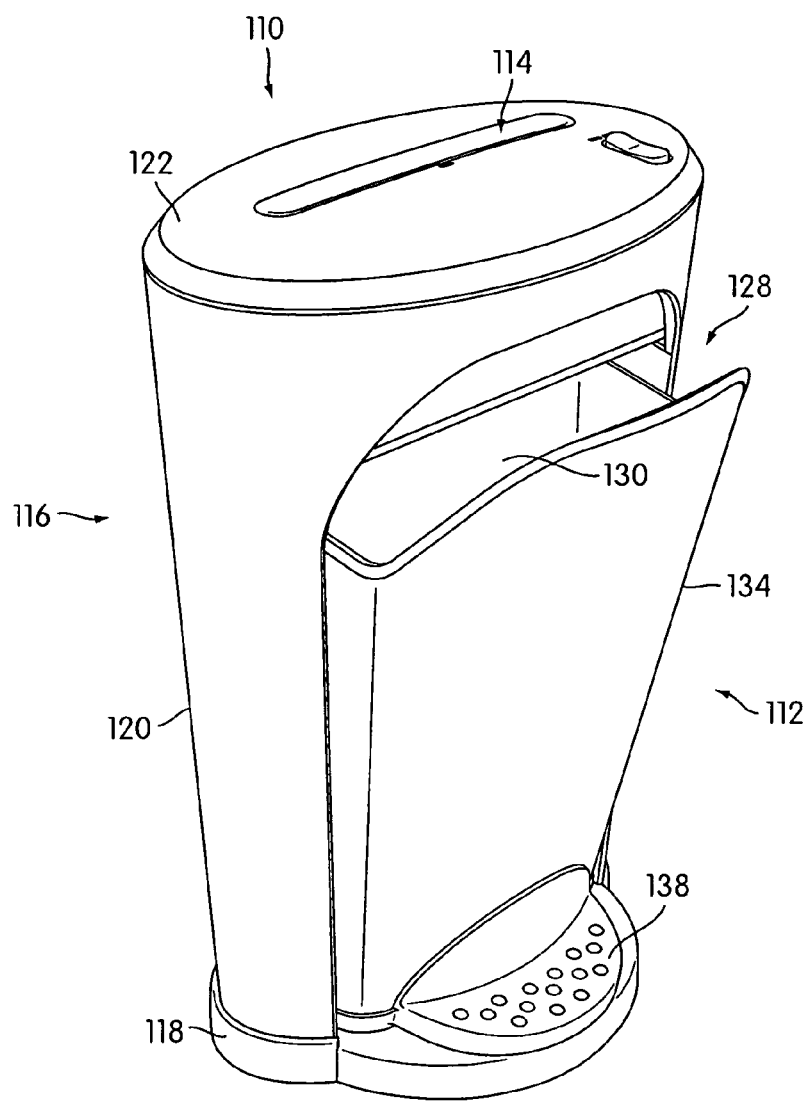
FIG. 12 is a top perspective view of the shredder of FIG. 11, with the waste receptacle in an open position.

FIGS. 11 and 12 illustrate another aspect of the present invention. FIG. 11 shows a shredder 110. The shredder 110 includes a waste receptacle 112 that has an interior waste receiving space that is suitable for receiving waste articles and objects, and a shredder mechanism 114 that is located above the waste receptacle 112. The shredder mechanism 114 may be of the type described above with respect to the shredder mechanism 14 that is shown in FIGS. 1–3 and will not be described in greater detail here.

The shredder 110 also includes a housing 116 that supports the shredder mechanism 114. The housing 116 includes a bottom portion 118 and a sidewall 120 that extends upward from the bottom portion 118 and at least partially surrounds the waste receptacle 112. As shown in FIG. 11, an upper portion 122 of the housing 116 is disposed substantially parallel to the bottom portion 118. The shredder mechanism 114 is disposed in the upper portion 122, or, alternatively, may be removably mounted to the sidewall 120 such that the shredder mechanism 114 defines the upper portion 122. The housing 116 and the waste receptacle 112 are constructed and arranged to define a closed position 124 in which the interior of the waste receptacle 112 may only receive shredded articles that have passed through the shredder mechanism 114.

The bottom portion 118 preferably includes a pivot (not shown) that is configured to allow the waste receptacle 112 to tilt outward and away from the housing 116 to an open position 128, as shown in FIG. 12, thereby creating a waste opening 130 that allows articles to enter the interior of the waste receptacle 112 without passing through the shredder mechanism 114. The open position 128 is defined as any position in which the waste opening 130 is created, and is not limited to a fully open position in which a maximum waste opening 130 is provided. A bottom surface of the waste receptacle 112 may also be configured to interact with the pivot such that the waste receptacle 112 is properly balanced when in both the closed position 124 and in the fully open position. It is also contemplated that the pivot may be provided on the bottom surface of the waste receptacle 112, instead of on the bottom portion 118.

When a person would like to dispose of an object and does not want the object to pass through the shredder mechanism 114, the person simply causes the waste receptacle 112 to tilt outward from the housing 116 to the open position 128 so that the waste opening 130 is created. The tilting of the waste receptacle 112 may be affected in at least two ways. First, an outer sidewall 134 of the waste receptacle 112 may include a handle (not shown) that is configured to be grasped by the person so that the person may simply pull the handle and tilt the waste receptacle 112 outward to the open position 128. Once the object is disposed of, the person may push the handle and/or the outer sidewall 134 towards the housing 116 and move the waste receptacle 112 back to the closed position 124. It is contemplated that the handle may be formed from a notch or recess in the sidewall 120 of the waste receptacle 112, or that the handle may be a separate piece that is attached to the exterior of the sidewall 120. Second, a foot pedal 138 may be provided on the bottom portion 118 of the housing 116 and be configured to receive the person's foot. The foot pedal 138 is operatively connected to the waste receptacle 112 so as to tilt the waste receptacle 112 about the pivot, thereby causing the waste receptacle 112 to tilt outward from the housing 116 when the foot pedal 138 is depressed. Such a configuration allows for hands-free interaction with the shredder 110 when disposing of objects that are not intended to be passed through the shredder mechanism 114.

Preferably, a sensor 140 for sensing when the waste receptacle 112 is in the open position 128 and is operatively connected to the shredder mechanism 114 is provided. The sensor 140 may be a mechanical or contact switch, an optical device, or any other mechanism that senses the position of the waste receptacle 112 and communicates that sensing to the shredder mechanism 114, thereby making the shredder mechanism 114 inoperable. The sensor 140 is also configured to sense when the waste receptacle 112 is in the closed position 124 and communicates that sensing to the shredder mechanism 114, thereby making the shredder mechanism 114 operable. The configuration of the shredder 110 is but one example of this aspect of the invention and should not be considered to be limiting in any way.

While preferred embodiments of the invention have been shown and described, it is evident that variations and modifications are possible that are within the spirit and scope of the following claims. The disclosed embodiments have been provided solely to illustrate the principles of the invention and should not be considered limiting in any way.

What is claimed is:

1. A shredder comprising:
   a waste receptacle having an interior waste receiving space;
   a shredder mechanism including a motor and cutter elements, the shredder mechanism enabling articles to be shredded to be fed into the cutter elements and the motor being operable to drive the cutter elements so that the cutter elements shred the articles therein, the shredder mechanism being positioned so that the shredded articles are discharged into the waste receiving space;
   the receptacle including a waste opening separate from the shredder mechanism for enabling articles to be discarded through the waste opening and received in the waste receiving space without passing through the shredder mechanism;
   a cover moveable between (1) a closed position that covers the waste opening, and (2) an open position that opens the waste opening; and
   a sensor for sensing the position of the cover and operatively connected to the shredder mechanism, the shredder mechanism being inoperable at least when the sensor senses that the cover is in the open position,
   wherein the waste receptacle has a base frame and a removable waste container providing the waste receiving space,
   the base frame including an upper portion on which the shredder mechanism is supported,
   the waste container being removably mounted beneath the upper portion to enable shredded articles from the shredder mechanism or articles discarded through the waste opening to be received in the waste receiving space,
   the removable mounting of the waste container enabling the waste container to be removed from the base frame out from underneath the upper portion for emptying, even when the cover is in the closed position.

2. A shredder according to claim 1, further comprising a foot pedal disposed at a bottom portion of the receptacle and operatively connected to the cover, the foot pedal being constructed and arranged to be actuated by a person's foot, wherein actuation of the foot pedal causes the cover to move to the open position.

3. A shredder according to claim 2, wherein a first link is operatively connected to the foot pedal and is disposed on the bottom portion of the receptacle, and a second link is operatively connected to the first link at one end and operatively connected to the cover at an opposite end, the first and second links being constructed and arranged to cause the cover to move to the open position when the foot pedal is actuated.

4. A shredder according to claim 1, wherein the receptacle comprises an upper wall, the shredder mechanism being provided on one portion of the upper wall, and the waste opening being provided on another portion of the upper wall.

5. A shredder according to claim 4, wherein the shredder mechanism is located below the one portion of the upper wall and wherein the one portion of the upper wall has a feed opening enabling the articles to be shredded to be fed into the shredder mechanism.

6. A shredder according to claim 5, wherein the cover comprises an opening that aligns with the feed opening when the cover is in the closed position such that the shredder mechanism is accessible when the cover is in the closed position.

7. A shredder according to claim 1, wherein the receptacle comprises an upper wall and wherein the shredder mechanism is located beneath the upper wall, the upper wall having a feed opening enabling the articles to be shredded to be fed into the shredding mechanism,
   wherein the cover comprises an opening that aligns with the feed opening in the closed position such that the shredder mechanism is accessible when the cover is in the closed position.

8. A shredder according to claim 1, wherein the cover comprises an opening that aligns with the shredder mechanism when the cover is in the closed position such that the shredder mechanism is accessible when the cover is in the closed position.

9. A shredder according to claim 1, wherein the receptacle comprises at least two compartments.

10. A shredder according to claim 9, wherein a first compartment receives shredded articles from the shredder mechanism, and a second compartment receives articles discarded through the waste opening.

11. A shredder according to claim 1, further comprising a second sensor for sensing the position of the removable waste container to the shredder mechanism, the shredder mechanism being inoperable at least when the second sensor senses that the removable waste container is removed.

12. A shredder according to claim 1, further comprising an electrically-powered air freshener.

13. A shredder according to claim 1, further comprising a liner frame that is constructed and arranged to support at least one removable liner within the receptacle, the liner frame comprising an outer rim that is configured so that the removable liner is removably clamped between the outer rim of the frame and the receptacle.

* * * * *